United States Patent [19]

Youngner, deceased

[11] Patent Number: Plant 5,845

[45] Date of Patent: Dec. 30, 1986

[54] ZOYSIAGRASS PLANT 'EL TORO'

[75] Inventor: Victor B. Youngner, deceased, late of Riverside, Calif., by Violet E. Youngner, heir

[73] Assignee: The Regents of the University of California, Berkeley, Calif.

[21] Appl. No.: 673,633

[22] Filed: Nov. 21, 1984

[51] Int. Cl.[4] ..... A01H 5/00

[52] U.S. Cl. ..... Plt./88

[58] Field of Search ..... Plt./88

*Primary Examiner*—R. E. Bagwill

*Attorney, Agent, or Firm*—Townsend and Townsend

[57] ABSTRACT

A new and distinct variety of Zoysia turfgrass (*Zoysia japonica*) characterized by its rapid establishment rate and shorter dormant period compared to other Zoysia varieties, its early spring greenup and good Fall color retention and further characterized by its superior tolerance to Zoysia rust (Puccinia Spp.) and high tolerance to drought.

4 Drawing Figures

The present invention relates to a new and distinct variety of Japanese lawn grass (*Zoysia japonica*). *Zoysia japonica* is a member of the Gramineae family and is commonly referred to by the names Zoysiagrass, Korean grass or Japanese lawn grass. It is native to Japan and is a common lawn grass normally requiring full sun.

This new cultivar of *Zoysia japonica,* which has been named 'El Toro,' was derived from open pollination among selected clones and was initially designated UCR #1. 'El Toro' has been propagated asexually by rhizomes and tillers. Following its initial observation it was placed in comparative observation plots with other selections at the University of California South Coast Field Station in 1978 and testing confirmed no noticeable differences between the asexually reproduced plants from the original selection, thus determining the integrity of the new variety.

The novelty of 'El Toro' primarily resides in its rapid establishment rate compared to other Zoysia varieties, i.e. two to three times that of other Zoysia varieties, its early spring greenup and good Fall color retention. 'El Toro' has a shorter dormant period and a superior tolerance to Zoysia rust (Puccinia Spp.). 'El Toro' produces numerous small (5- to 6-cm high) inflorescences in spring and early summer which are readily removed by mowing and detract little from turf appearance. An important characteristic of the new variety is its high tolerance to drought. Its prostrate growth habit and slow rate of leaf elongation necessitate mowing only every 7–14 days depending on season and use requirements.

'El Toro,' like other zoysiagrass varieties, normally requires full sun. It is hardy to zone 7 (0° to 10 degrees F.), though it is better adapted to more southern climates as it tends to turn brown and go dormant under frost and cool night temperatures. In this respect 'El Toro' is similar to some of the hybrid burmudagrass selections.

A primary object of the invention is to provide a new and distinct variety of Zoysiagrass plant having the desirable characteristics referred to above and to be described in detail below.

Other objects and advantages of the invention will become more fully apparent from the following detailed description when taken in conjunction with the accompanying illustrations in which.

Figure 1:
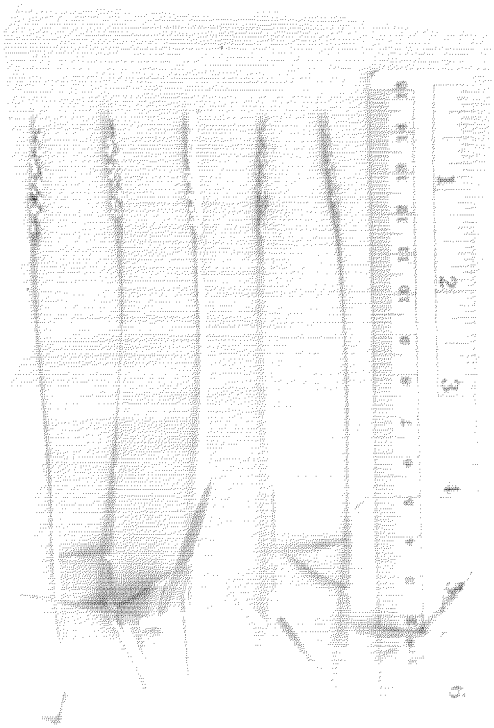
FIG. 1 shows a typical panicle of the variety.
Figure 2:
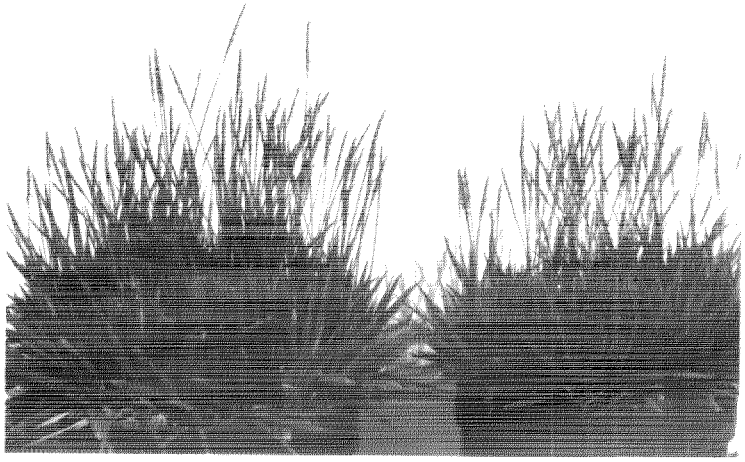
FIG. 2 shows a clump of the variety after completion of flowering.
Figure 3:
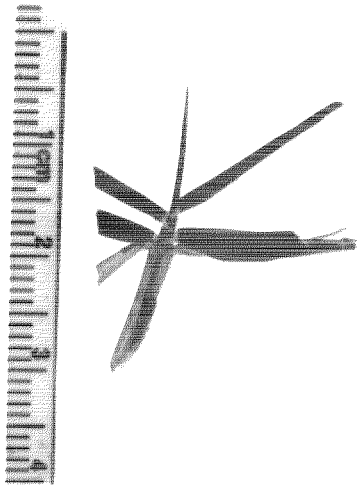
FIG. 3 shows a typical tiller of the variety extracted from a closely mowed turf.
Figure 4:
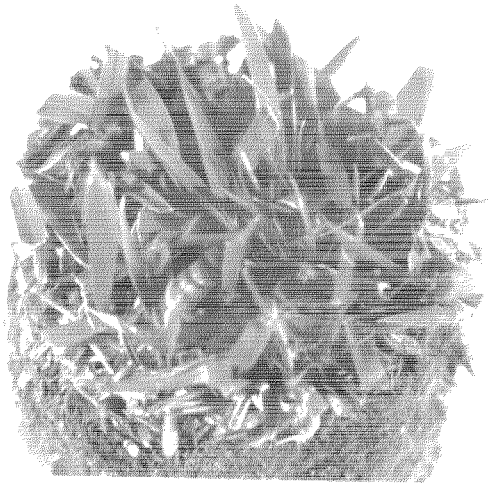
FIG. 4 is a three-fourths view of a clump of closely mowed turf of the variety.

Testing with adequate cultural practices has proved the merit of 'El Toro' due to its vigor, its ability to spread and the quality of the established turf. Although somewhat coarse in texture, and while it is thought that the new variety is suitable for home lawns, it appears best suited for athletic fields and possibly parks and golf courses. 'El Toro' has not been stress tested under field conditions and, at present, its recovery period after stress is not known.

The 'El Toro' variety is sold either as rolled in sod, as stolons for broadcasting, or in flats for plugging. Commercial seeding is normally not practiced, most likely due to problems with viable seed set or to germination problems.

PLANT DESCRIPTION

Under conditions such as those experienced in 1978 at the University of California South Coast Field Station, the following plant descriptions of 'El Toro' can be made best on average measurements:

Leaf — Blades are flat, obtuse, usually 13–23 cm long, about 3 mm wide or more.

Racemes — Spikelike, usually 2.5 cm long, and spikelets are about 3 mm long, pale, purplish-brown.

Inflorescence — Numerous, small, 5- to 6-cm high — produced in spring and early summer.

Hardiness — Hardy to zone 7 (0 to 10 degrees F.), though adapted to more southern climate, tends to turn brown an go dormant under frost and cool night temperatures.

It is claimed:

1. The new and distinct variety of Zoysiagrass plant herein described and illustrated and identified by the characteristics enumerated above.

* * * * *